United States Patent [19]

von König et al.

[11] 4,396,707
[45] Aug. 2, 1983

[54] PHOTOGRAPHIC MATERIAL, PROCESS FOR THE PRODUCTION THEREOF, PROCESS FOR THE PRODUCTION OF PHOTOGRAPHIC IMAGES AND NEW TRIAZOLES

[75] Inventors: Anita von König, Krefeld; Werner Liebe, Leverkusen; Wilhelm Saleck, Bergisch Gladbach, all of Fed. Rep. of Germany

[73] Assignee: Agfa-Gevaert Aktiengesellschaft, Leverkusen, Fed. Rep. of Germany

[21] Appl. No.: 295,756

[22] Filed: Aug. 24, 1981

[30] Foreign Application Priority Data

Sep. 2, 1980 [DE] Fed. Rep. of Germany ....... 3032945

[51] Int. Cl.³ .............................................. G03C 1/34
[52] U.S. Cl. .................................. 430/446; 430/448; 430/569; 430/614; 430/551; 548/263
[58] Field of Search ............... 430/611, 569, 434, 551, 430/614, 446, 448; 548/263

[56] References Cited

U.S. PATENT DOCUMENTS 3,311,474 3/1967 Willems et al. ...................... 430/611
3,640,719 2/1972 von Konig et al. ................. 430/614

FOREIGN PATENT DOCUMENTS 1186441 4/1970 United Kingdom ................ 430/611

Primary Examiner—Won H. Louie, Jr.
Attorney, Agent, or Firm—Connolly and Hutz

[57] ABSTRACT

New triazoles of the formula

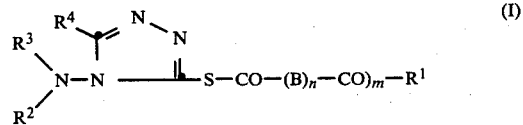

are suitable stabilizing agents in photographic materials.

8 Claims, No Drawings

PHOTOGRAPHIC MATERIAL, PROCESS FOR THE PRODUCTION THEREOF, PROCESS FOR THE PRODUCTION OF PHOTOGRAPHIC IMAGES AND NEW TRIAZOLES

This invention relates to a photographic material containing a stabilizing agent, to a process for the production of this material, to a process for the production of photographic images and to new triazoles. The present invention relates in particular to a photographic material containing at least one silver halide emulsion layer which has been stabilized against fogging, in particular against the formation of colour fog, by the addition of the stabilizers according to the present invention.

Materials containing light-sensitive silver halide emulsions, in particular those which have been chemically sensitized, are known to be subject to fogging due to the presence of nuclei which are capable of being developed without exposure to light. This fogging is particularly liable to occur in the course of prolonged storage, especially at elevated temperatures and in the presence of atmospheric moisture, or if development is carried out for too long or at too high a temperature, or in the presence of certain additives or if the emulsions are strongly ripened.

When photographic materials are rapidly processed at temperatures above 30° C. and development and fixing or bleach fixing times of less than 6 minutes in the individual baths are used, fogging is frequently more pronounced than in conventional slower development processes carried out at 20° C.

It is known to add so-called "anti-fogging agents" or stabilizers to photographic silver halide emulsions to reduce this fogging. Compounds which have such a stabilizing action include, for example, heterocyclic compounds containing sulphur, for example in the form of a mercapto group. Examples may be found in German Auslegeschrift Nos. 1,183,371; 1,189,380; 1,597,503; and 1,797,027, and German Offenlegungsschrift Nos. 1,522,363; 2,042,533; 2,130,031; 2,308,530 and 2,943,673.

The usefulness of these stabilizers, is however, limited by the fact that, when used in effective concentrations, they sometimes reduce the sensitivity of the stabilized emulsion. The gradation of the emulsion may also be adversely affected by these stabilizers.

In the course of processing of the stabilized photographic material, stabilizer is liable to be carried over into the developer and/or the bleach fix bath, even if only in very small quantities. When these photographic materials are processed in large quantities, the compounds accumulate in the developer and/or bleach fix bath. The accumulation thereof in the developer has the disadvantage of reducing the speed of development or, in the case of light-sensitive colour photographic multi-layered material, it may destroy the colour balance. The accumulation in the bleach fix bath has the disadvantage of reducing the speed of bleaching so that at the short bleach fixing times required for rapid processing of photographic materials a fog is produced by silver which has failed to be removed.

Both these disadvantages are particularly pronounced if a recovered or regenerated developer is used and/or a recovered and regenerated bleach fix bath.

It is an object of the present invention to provide stabilizers which stabilize photographic materials against the formation of fog and colour fog, in particular when processing is carried out at elevated temperatures, and which do not delay either development or bleaching even when recovered and regenerated processing baths are used.

A further object of the present invention is the preparation of photographic materials containing at least one silver halide emulsion layer which is stabilized using these compounds. Further objects will emerge from the description.

The following have now been found:

(1) A photographic material comprising a layer support and at least one light-sensitive silver halide emulsion layer applied to this support and optionally also further layers, at least one layer containing a compound corresponding to the following general formula (I):

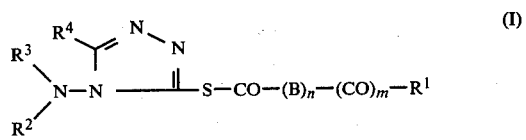

in which

R$^1$ denotes an optionally substituted alkyl, cycloalkyl, aryl or aralkyl group or a substituted triazole group linked via an —S— atom R$^2$ denotes H, acyl, alkyl or —COOR$^5$ R$^3$ denotes H, acyl or —COOR$^5$ R$^4$ denotes H or alkyl R$^5$ denotes alkyl, cycloalkyl, aryl, aralkyl n and m, which are the same or different, denote 0 or 1 and B denotes a divalent linking member (2) A process for the preparation of a photographic material containing at least one silver halide emulsion layer by precipitation of the silver halide in the presence of a protective colloid, optional physical and chemical ripening and application of the resulting casting solution to a layer support, characterised in that compounds corresponding to general formula (I) are added before chemical ripening and/or at latest to the casting solution.

(3) A process for the production of photographic images by image-wise exposure and development of the material according to the present invention, and (4) New compounds corresponding to general formula (I) above.

R$^1$ is preferably an alkyl group with 1–6 C atoms, in particular methyl, ethyl, isopropyl, butyl or a cycloalkyl group with 5 or 6 C atoms, in particular cyclohexyl or a phenyl group or a benzyl group or a group of the formula

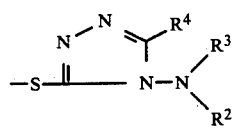

in which R$^2$–R$^4$ have the abovementioned meaning

R$^2$ is preferably H, acetyl, alkyl with 1–4 C atoms or COOR$^5$

R$^3$ is preferably H or an acyl group. A particularly preferred acyl group is the acetyl group.

R$^4$ preferably denotes H or an alkyl group with 1–4 C atoms in particular methyl or ethyl.

$R^5$ preferably denotes alkyl with 1-6 C atoms or cycloalkyl with 5 or 6 C atoms, in particular cyclohexyl or phenyl or benzyl.

The linking member B is preferably —O— or an organic group, in particular an alkylene group, in particular one having from 1 to 6 C atoms, an arylene group, in particular a phenylene group, a cycloalkylene group, in particular one having 5 or 6 C atoms or an aralkylene group, in particular a group of the formula

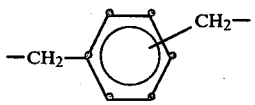

When B is an organic group it can carry an oxygen atom either at one or at two positions, preferably as terminal atoms.

Specific examples for B are:
—O—
—O—[CH$_2$]$_p$—O— in which p=1-4
—[CH$_2$]$_p$— in which p=1-4

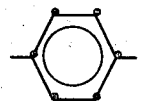

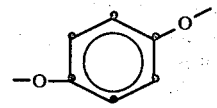

In a preferred embodiment the linking member B is an organic group and n=1 when m=1.

The indicated substituents may in turn be substituted by the conventional substituents used for stabilizers in the photographic field, for example by halogen, alkoxy, cyano, carboxyl or COOR$^5$.

Particularly suitable compounds corresponding to general formula (I) are shown in Table 1 below:

TABLE 1

| No. | —(B)$_n$—(CO)$_m$—R$^1$ | R$^2$ | R$^3$ | R$^4$ |
|---|---|---|---|---|
| 1.1 | CH$_3$ | CO—CH$_3$ | H | H |
| 1.2 | O—C$_4$H$_9$—n | CO—O—C$_4$H$_9$—n | H | H |
| 1.3 | O—C$_2$H$_5$ | CO—O—C$_2$H$_5$ | CO—CH$_3$ | H |
| 1.4 | O—C$_4$H$_9$—n | CO—O—C$_4$H$_9$—n | CO—CH$_3$ | H |
| 1.5 | O—C$_4$H$_9$—iso | CO—O—C$_4$H$_9$—iso | CO—CH$_3$ | H |
| 1.6 | O—C$_2$H$_5$ | CO—O—C$_2$H$_5$ | COO—C$_2$H$_5$ | H |
| 1.7 | [triazole-S— with NH—CO—CH$_3$] | CO—CH$_3$ | H | H |
| 1.8 | CH$_3$ | CO—CH$_3$ | H | CH$_3$ |
| 1.9 | O—C$_2$H$_5$ | CO—O—C$_2$H$_5$ | CO—CH$_3$ | CH$_3$ |
| 1.10 | O—C$_4$H$_9$—n | CO—O—C$_4$H$_9$—n | CO—CH$_3$ | CH$_3$ |
| 1.11 | O—C$_4$H$_9$—n | H | H | CH$_3$ |
| 1.12 | [O-cyclohexyl-H] | [CO—O-cyclohexyl-H] | H | CH$_3$ |
| 1.13 | O—CH(CH$_3$)$_2$ | CO—O—CH(CH$_3$)$_2$ | CO—CH$_3$ | CH$_3$ |
| 1.14 | O—C$_4$H$_9$—iso | CO—O—C$_4$H$_9$—iso | CO—CH$_3$ | CH$_3$ |
| 1.15 | O—C$_4$H$_9$—n | CO—O—C$_4$H$_9$—n | H | CH$_3$ |
| 1.16 | [H$_3$C-triazole-S— with NH—CO—CH$_3$] | CO—CH$_3$ | H | CH$_3$ |
| 1.17 | [O-cyclohexyl-C(CH$_3$)$_3$, H] | [CO—O-cyclohexyl-C(CH$_3$)$_3$, H] | H | CH$_3$ |
| 1.18 | [triazole-S—CO—O—[CH$_2$]$_2$—O— with NH—COCH$_3$] | CO—CH$_3$ | H | H |

TABLE 1-continued

| No. | $-(B)_n-(CO)_m-R^1$ | $R^2$ | $R^3$ | $R^4$ |
|---|---|---|---|---|
| 1.19 | ![triazole]-S-CO-[CH$_2$]$_4$- (N=N, N-NH-CO-CH$_3$) | CO-CH$_3$ | H | H |
| 1.20 | ![triazole]-S-CO-phenyl (N=N, N-NH-COCH$_3$) | COCH$_3$ | H | CH$_3$ |
| 1.21 | -O-cyclohexyl-H | COO-cyclohexyl-H | COCH$_3$ | H |
| 1.22 | O-C$_4$H$_9$-iso | COO-C$_4$H$_9$-iso | H | H |
| 1.23 | O-C$_2$H$_5$ | | H | H |
| 1.24 | O-cyclohexyl-H | COO-cyclohexyl-H | COCH$_3$ | CH$_3$ |
| 1.25 | CH$_3$ | COCH$_3$ | H | C$_2$H$_5$ |
| 1.26 | O-C$_2$H$_5$ | COO-C$_2$H$_5$ | H | C$_2$H$_5$ |
| 1.27 | ![triazole]-N-S-CO-(methylcyclohexyl) (N=N, N-NH-CO-CH$_3$) | CO-CH$_3$ | H | H |
| 1.28 | ![triazole]-N-S-CO-CH$_2$-phenyl-CH$_2$- (N=N, N-NH-CO-CH$_3$) | CO-CH$_3$ | H | H |

The compounds corresponding to general formula (I) may be prepared by known methods. Compound 1.1 is obtained from the underlying 3-mercapto-4-amino-1,2,4-triazole and compound 1.8 is prepared from thiocarbohydrazide by ring closure and acylation using acetic acid anhydride in glacial acetic acid. Compounds 1.2 to 1.6, 1.9 to 1.15 and 1.17 to 1.28 are prepared by reaction of the underlying 3-mercapto-4-amino-1,2,4-triazole with chloroformic acid esters, pyrocarbonic acid esters or acid chlorides, preferably in diluents, as described in German Pat. No. 1,189,380 and German Offenlegungsschrift No. 2,042,533.

Compounds 1.7 and 1.16 are prepared in known manner by reaction with phosgene in a diluent in the presence of alkali, as described in German Pat. No. 1,797,027. The preparation of some of the compounds is described in detail below; the other compounds are obtained in analogous manner.

Preparation of Compound 1.1

A suspension of 23.2 g (0.2 mol) of 3-mercapto-4-amino-1,2,4-triazole is heated to boiling in 70 ml of glacial acetic acid with stirring. 56.7 ml of acetic acid anhydride are added dropwise to the boiling solution and the solution is stirred at boiling point for 30 minutes. After cooling, the reaction mixture is suction filtered and the product is purified by repeated precipitation from acetone and petroleum ether. Yield: 10.4 g; Decomposition point: 128° to 130° C.

Preparation of Compound 1.4

40 ml of 5 N sodium hydroxide solution are added with stirring to a suspension of 15.8 g (0.1 mol) of 3-mercapto-4-acetylamino-1,2,4-triazole in 300 ml of acetone. 27.1 ml of chloroformic acid-n-butyl ester dissolved in 100 ml of anhydrous acetone are slowly added dropwise at from 0° to 5° C. After 4 hours stirring at room temperature, the precipitated salt is suction filtered and the solution concentrated by evaporation under vacuum. The oily residue is dissolved in ether, washed, stirred with aluminium oxide and active charcoal and dried, the ether is then distilled off. The oily substance is purified by dissolving it repeatedly in chloroform and ethyl acetate and treating the solutions with active charcoal and aluminium oxide. Yield: 7.5 g of viscous oil.

Results of analysis:

| | % calculated | % observed |
|---|---|---|
| C | 47.0 | 47.2; 47.1 |
| H | 6.17 | 6.2  6.3 |

|   | % calculated | % observed |
|---|---|---|
| N | 15.62 | 15.7 |
| O | 22.31 | 22.1 |
| S | 8.94 | 9.2 |

Preparation of Compound 1.8

A suspension of 21.23 g (0.2 Mol) of thiocarbohydrazide is heated to boiling in 100 ml of glacial acetic acid with stirring and exclusion of moisture.

85.05 ml (0.9 mol) of acetic acid anhydride are added dropwise to the boiling solution. The reaction mixture is boiled for 5 hours with stirring and then evaporated to dryness under a water jet vacuum. After cooling the product to from 25° to 30° C., 30 ml of acetone are added and the mixture is vigorously stirred; the product becomes crystalline. After suction filtration, the product is stirred with water, vigorously suction filtered and then stirred twice with acetone. The product is subsequently dried over $P_2O_5$ in a vacuum drying stove at room temperature. Yield: 16.5 g; Decomposition point: 176° to 180° C.

| The following NMR $^{13}C$ shifts were found: | |
|---|---|
| NMR $^{13}C$ shifts | (ppm, relative to TMS = O) |
| C-3 | 166.707 |
| $CH_3$ on C-5 | 9.845 |
| C-5 | 149.818 |
| CO of NHAc | 168.423 |
| $CH_3$ of NHAc | 20.304 |
| CO of SAc | 167.088 |
| $CH_3$ of SAc | 24.173 |

Preparation of Compound 1.9

40 ml of 5 N sodium hydroxide solution are added with stirring to a suspension of 17.2 g (0.1 mol) of 3-mercapto-4-acetylamino-5-methyl-1,2,4-triazole in 200 ml of acetone. 21 ml of ethyl chloroformate dissolved in 100 ml of anhydrous acetone are added dropwise at from 0° to 5° C. After 4 hours stirring at room temperature, the precipitated salt is filtered and the solution concentrated by evaporation under vacuum. The residue is dissolved in 100 ml of acetone and the solution is treated with active charcoal. After removal of the acetone by distillation under vacuum, the product is stirred several times with petroleum ether and ether. Yield: 7.8 g; Decomposition point: 98° to 99° C.

Preparation of compound 1.10

60 ml of 5 N sodium hydroxide solution are added dropwise to a solution of 21.4 g (0.1 mol) of compound 1.8 in 100 ml of acetone with stirring. 27.1 ml of chloroformic acid-n-butyl ester dissolved in 100 ml of anhydrous acetone are added dropwise at from 0° to 5° C. After 3 hours stirring at room temperature, the precipitated salt is filtered off and the solution is concentrated by evaporation under vacuum. The residue is dissolved in ether, washed, stirred with aluminium oxide and active charcoal and dried, the ether is then distilled off. The oil is purified by repeatedly dissolving it in acetone and treating it with active charcoal and aluminium oxide. Yield: 21.5 g of viscous oil.

Results of analysis:

|   | % calculated | % observed |
|---|---|---|
| C | 48.37 | 48.3; 48.4 |
| H | 6.50 | 6.2; 6.3 |
| N | 15.04 | 15.6; 15.6 |
| O | 21.48 | 21.6 |
| S | 8.61 | 8.7 |

The sensitivity which may be obtained in a photographic material by means of the stabilizers according to the present invention is very high and is not reduced by storage. This stability of a photographic material, which is very important in the art, is achieved to an outstanding degree by using the compounds according to the present invention. The fog which is normally formed in the course of development is supressed.

The compounds according to the present invention are advantageously added in the form of solutions. Suitable solvents include, for example, lower alcohols, tetrahydrofuran and acetone.

The emulsions may contain other stabilizers in combination with the stabilizers according to the present invention. Suitable additional stabilizers include azaindenes, particularly tetra- and penta-azaindenes, and especially those which are substituted with hydroxyl or amino groups. Compounds of this type have been described in the article by Birr, Z. wiss. Phot., 47, 2–58 (1952). Other suitable stabilizers include, inter alia, heterocyclic mercapto compounds, e.g. phenyl mercapto tetrazole, quaternary benzothiazole derivatives, benzotriazole and the like.

Particularly preferred additional stabilizers of the azaindene series are shown in Table 2:

TABLE 2

| No. | Compound |
|---|---|
| 2.1 | 4-hydroxy-6-methyl-1,3,3a,7-tetraazaindene, |
| 2.2 | 4-hydroxy-5-carboxy-1,3,3a,7-tetraazaindene, |
| 2.3 | 4-hydroxy-5-carbethoxy-1,3,3a,7-tetraazaindene, |
| 2.4 | 2-β-hydroxyethyl-4-hydroxy-6-methyl-1,3,3a,7-tetraazaindene, |
| 2.5 | 2-methyl-4-hydroxy-1,3,3a,7-tetraazaindene, |
| 2.6 | 4-hydroxy-6-methyl-1,2,3,3a,7-pentaazaindene. |

The stabilizers according to the present invention may be added to the light-sensitive silver halide emulsions before chemical ripening or at or after the stage of chemical ripening. In a preferred embodiment, they are added to the finished casting solution after chemical ripening.

The stabilizers according to the present invention are preferably added to the light-sensitive silver halide emulsions before or after chemical ripening. They may, of course, also be added to other photographic layers. The concentration of the stabilizers in the emulsion may vary within wide limits and depends on the nature of the emulsion and the desired effect. Quantities of from 5 to 500 mg, in particular from 10 to 200 mg, per mol of silver halide generally produce the desired effects.

The optimum quantity to be added to a given emulsion may easily be determined by the conventional tests.

Additional stabilizers may in principle be added to the photographic materials or emulsions before, after or during addition of the stabilizers according to the present invention.

The conventional silver halide emulsions are suitable for the present invention. The silver halide contained in them may be silver chloride, silver bromide or mixtures thereof, optionally with a small silver iodide content of up to 10 mol percent.

The binder used for the photographic layers is preferably gelatine, although this may be partly or completely replaced by other natural or synthetic binders.

The emulsions may also be chemically sensitized, e.g. by adding to them, at the stage of chemical ripening, sulphur compounds, such as allyl isothiocyanate, allylthio urea or sodium thiosulphate. Reducing agents may also be used as chemical sensitizers, e.g. the tin compounds described in Belgian Pat. Nos. 493,464 and 568,687, polyamines, such as diethylene triamine or aminomethyl sulphinic acid derivatives, e.g. according to Belgian Pat. No. 547,323. Noble metals, such as mold, platinum, palladium, iridium, ruthenium or rhodium, and compounds of these metals are also suitable chemical sensitizers. The emulsions may also be sensitized using polyalkylene oxide derivates, e.g. polyethylene oxides having molecular weights of from 1,000 to 20,000, or using condensation products of alkylene oxides and alcohols, aliphatic carboxylic acids, aliphatic amines, aliphatic diamines or amides.

The emulsions may also be optically sensitized, e.g. using the conventional polymethine dyes, such as neutrocyanines, basic or acid carbocyanines, rhodacyanines, hemicyanines, styryl dyes, oxonoles and the like. Sensitizers of this type have been described in the work by F. M. Hamer "The Cyanine dyes and related Compounds", (1964).

A particularly advantageous effect is shown by the stabilizers according to the present invention in silver halide emulsions which contain colour couplers since the presence of colour couplers is frequently known to reduce severely the effect of other, known stabilizers so that where silver halide emulsions containing colour couplers are present in a photographic material it is particularly difficult to obtain sufficient stability in storage and sufficient freedom from fogging if development times are long or the development temperatures are high. When using the stabilizers according to the present invention, excellent stabilisation even of silver halide emulsions containing colour couplers is obtained under conditions of prolonged storage and development at elevated temperatures.

The photographic material prepared according to the present invention may contain the conventional colour couplers which generally are directly incorporated in the silver halide layers. The red-sensitive layer, for example, contains a non-diffusible colour coupler to produce the cyan partial colour image, generally a coupler of the phenol or α-naphthol series; the green-sensitive layer contains at least one non-diffusible colour coupler to produce the magenta partial colour image, these colour couplers being generally of the 5-pyrazolone or indazolone series, while the blue-sensitive layer unit contains at least one non-diffusible colour coupler to produce the yellow partial colour image, generally a colour coupler having an open-chain ketomethylene group. Colour couplers of this type are known in large numbers and have been described in numerous patent specifications and other publications, for example in "Farbkuppler" by W. Pelz in "Mitteilungen aus den Forschungslaboratorien der Agfa, Leverkusen/Munchen", Volume III (1961) and by K. Venkataranam in "The Chemistry of Synthetic Dyes", Volume 4, pages 341 to 387, Academic Press, 1971.

2-equivalent couplers may also be used as non-diffusible colour couplers. These contain a removable substituent in the coupling position so that, in contrast to the conventional 4-equivalent couplers, they require only 2 equivalents of silver halide to produce the colour. Suitable 2-equivalent couplers include, for example, the known DIR couplers in which the removable group is released as diffusible development inhibitor after the reaction with colour developer oxidation products. So-called "white couplers" may also be used to improve the properties of the photographic material.

It is particularly advantageous to use the stabilizers according to the present invention together with 2-equivalent α-acyl-acetamide yellow couplers. Particularly advantageous couplers of this type are the pivaloyl yellow couplers corresponding to general formula (II):

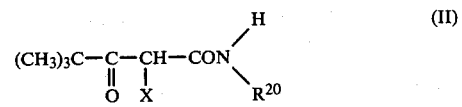

(II)

wherein
R$^{20}$ represents an aryl group (in particular a phenyl or naphthyl group or the like) or a heterocyclic group (in particular a thienyl, benzothienyl, furyl, pyranyl, pyrrolyl, imidazolyl, pyrazolyl, pyridyl, pyrimidyl, pyridazyl, indolyl, indazolyl, quinolyl, oxazolyl, pyrrolidyl, benzoimidazolyl, naphthoimidazoyl, benzoxazolyl, naphthoxazolyl, thiazolyl, benzothiazolyl, naphthothiazolyl, selenazolyl or benzoselenazolyl group or the like); and
X represents a group corresponding to the general formula:

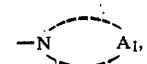

wherein A$_1$ represents a group of non-metallic atoms required to form a from 4- to 6-memebered heterocyclic ring which contains nitrogen and may in addition contain a nitrogen, oxygen or sulphur atom as heteroatom or a substituent.

The non-diffusible colour couplers and colour producing compounds are added to the light-sensitive silver halide emulsions or other casting solutions by the conventional methods. If the compounds are soluble in water or alkalies, they may be added to the emulsions in the form of aqueous solutions, optionally with the addition of water-miscible organic solvents, such as ethanol, acetone or dimethylformamide. If, on the other hand, the non-diffusible colour couplers and colour producing compounds are insoluble in water and alkalies, they may be emulsified in known manner, for example by directly mixing a solution of these compounds in a low boiling organic solvent with the silver halide emulsion or by first mixing it with an aqueous gelatine solution and then removing the organic solvent in the conventional manner. A gelatine emulsion of the compound thus obtained in subsequently mixed with the silver halide emulsion. So-called "coupler solvents" or oil-formers may in addition be used for emulsifying such hydrophobic compounds. These coupler solvents or oil-formers are generally organic compounds having a relatively high boiling point which enclose in the form of oily droplets of non-diffusible colour couplers and development inhibitor releasing compounds which are to be emulsified in the silver halide emulsions. Information on this subject may be found, for example, in U.S. Pat. Nos. 2,322,027; 2,533,514; 3,689,271; 3,764,336 and 3,765,897.

The photographic materials may be developed using the conventional black and white developers, e.g. hydroquinone, pyrocatechol, p-methylamino phenol and 1-phenyl-3-pyrazolidone, and using colour developer substances, in particular of the p-phenylene diamine series, e.g. with N,N-dimethyl-p-phenylene diamine, 4-amino-3-methyl-N-ethyl-N-methoxyethyl aniline, 2-amino-5-diethylamino toluene, N-butyl-N-ω-sulphobutyl-p-phenylene diamine, 2-amino-5-(N-ethyl-N-β-methane sulphonamidoethyl-amino)-toluene, N-ethyl-N-β-hydroxyethyl-p-phenylene diamine, N,N-bis-(β-hydroxyethyl)-p-phenylene diamine and 2-amino-5-(N-ethyl-N-β-hydroxyethylamino)-toluene. Other suitable colour developers have been described in, for example, J. Amer. Chem. Soc. 73, 3100 (1951).

The layers of the photographic material may be hardened in the conventional manner, for example using formaldehyde or halogen-substituted aldehydes containing a carboxyl group, such as mucobromic acid, diketones, methane sulphonic acid esters, dialdehydes and the like. The photographic layers may also be hardened using epoxide hardeners, heterocyclic ethylene imine hardeners or acryloyl hardeners. They may also be hardened by the process according to German Offenlegungsschrift No. 2,218,009 to produce colour photographic materials which are suitable for high temperature processing. The photographic layers of colour photographic multi-layered materials may also be hardened using hardeners of the diazine, triazine or 1,2-dihydroquinoline series. Examples of such hardeners include diazine derivatives containing alkyl sulphonyl or aryl sulphonyl groups, derivatives of hydrogenated diazines or triazines, e.g. 1,3,5-hexahydrotriazine, fluoro-substituted diazine derivatives, e.g., fluoropyrimidine, and esters of 2-substituted 1,2-dihydroquinoline- or 1,2-dihydroisoquinoline-N-carboxylic acids. Vinyl sulphonic acid hardeners and carbodiimide and carbamoyl hardeners are also suitable, e.g. those described in German Offenlegungsschrift Nos. 2,263,602; 2,225,230 and 1,808,685, French Pat. No. 1,491,807 German Pat. No. 872,153 and DDR Pat. No. 7218. Other suitable hardeners have been described in, for example, British Pat. No. 1,268,550.

EXAMPLES

The following Examples explain the present invention without restricting it to the various embodiments in the Examples.

The comparison substances used in these Examples are the following known stabilizers:

Summary

| | Compound | disclosed in |
|---|---|---|
| A | 3-acetylthio-5-amino-1,2,4-triazole | |
| B | 3-acetylthio-4-acetyl-5-amino-1,2,4-triazole | |
| C | 3-ethoxycarbonylthio-5-ethoxycarbonylamino-1,2,4-triazole | German Patent No. 1,522,363, Compound 27 |
| D | 1-phenyl-5-mercapto-1,2,3,4-tetrazole | |
| E | 3-mercapto-4-amino-1,2,4-triazole | Japanese Patent No. 78/17492 and |
| F | 3-mercapto-4-acetylamino-1,2,4-triazole | Japanese Patent No. 75/539 |

-continued

| | Compound | disclosed in |
|---|---|---|
| G | 3-mercapto-4-amino-5-methyl-1,2,4-triazole | " |
| H | 3-mercapto-4-acetylamino-5-methyl-1,2,4-triazole | " |
| I | 3-mercapto-1-phenyl-5-acetylamino 1,2,4-triazole | German Offenlegungsschrift No. 2,308,530 |
| J | 4-(p-sulpho-anilino)-5-methyl-3-mercapto-1,2,4-triazole | German Patent No. 1,183,371 |
| K | 1-phenyl-3-mercapto-1,2,4-triazole | |

EXAMPLE 1

A highly sensitive silver iodo-bromide emulsion having an iodide content of 5 mol percent and a gelatine: silver ratio of 1.2 and containing 85 g of silver nitrate per kg of emulsion were ripened to optimum sensitivity using sulphur and gold compounds.

The emulsion was divided into several parts and the following substances were added per kg of emulsion:

| | |
|---|---|
| 4-hydroxy-6-methyl-1,3,3a,7-tetraazaindene 1% aqueous alkaline solution | 150 mg |
| Saponin 10%, dissolved in water | 3.5 g | and the substances according to the present invention (as 1% solutions in acetone or methanol) shown in the following Table were added in the quantities indicated. The quantities used were calculated to ensure that no substantial reduction in sensitivity occurred.

The emulsions were then cast on a cellulose acetate support and dried (amounts applied, from 6.8 to 7.0 g, calculated as silver nitrate per m$^2$). A protective layer containing a suitable hardener and a wetting agent was applied to each emulsion layer in a thickness corresponding to 2 g of gelatine per m$^2$. The samples were tested fresh and after storage in a heating cupboard at 60° C. for 3 days.

The samples were then exposed behind a grey wedge in a sensitometer and developed for 6 minutes at 38° C. in a developer I having the composition indicated below. This developer, which contains a silver complex former, is typical of a black and white developer for the reversal processing of photographic materials.

| Developer I | | |
|---|---|---|
| 4-hydroxymethyl-4-methyl-1-phenyl-3-pyrazolidone | 1.4 | g |
| sodium bicarbonate sicc. | 12 | g |
| diethylene glycol | 12 | ml |
| potassium hydroxide 45% | 7 | ml |
| potassium iodide | 4.5 | mg |
| potassium hydroquinone sulphonate | 22 | g |
| potassium carbonate sicc | 14 | g |
| potassium sulphite 45% | 44 | ml |
| potassium thiocyanate sicc | 1 | g |
| potassium bromide | 2.2 | g |
| Na$_6$ salt of nitrilo-trimethylene triphosphonic acid | 1 | ml |
| made up with water to 1 liter and adjusted to pH 9.6. | | |

The material is then treated in a stop bath consisting of 10 g of sodium acetate sicc. and 20 g of 96% glacial acetic acid in 1 liter of water. It is then fixed in a 15% ammonium thiosulphate and 1% sodium sulphite solution and washed. The results of sensitometric examination are shown in Table 3.

To test for fogging, an unexposed sample is developed for 6 minutes in developer I at 38° C.

Subsequent processing is carried out as indicated above. The fogging produced is entered in Table 3 as "percentage fogging" which is obtained by dividing the quantity of developed silver (as silver nitrate) by the quantity of silver (as silver nitrate) before processing a multiplying the quotient by 100.

It may be seen from this Table that these substances reduce fogging, particularly that produced in the heating cupboard, and are therefore suitable as anti-fogging agents for reversal materials.

TABLE 3

| Compound No. | mg/kg | Fresh sample sensitivity* | γ | % fogging | Heating cupboard sample sensitivity* | γ | % fogging |
|---|---|---|---|---|---|---|---|
| Control sample | — | 41.0 | 0.73 | 41 | 40.6 | 0.68 | 57 |
| 1.1 | 40 | +0.4° | 0.69 | 18 | +1.4° | 0.68 | 26 |
| 1.8 | 21 | ±0° | 0.69 | 20 | +0.8° | 0.67 | 28 |
| 1.8 | 43 | +0.7° | 0.64 | 11 | +1.3° | 0.65 | 13 |
| 1.9 | 63 | +0.7° | 0.75 | 26 | +0.4° | 0.69 | 25 |
| 1.9 | 127 | −0.8° | 0.71 | 13 | ±0° | 0.67 | 12 |
| 1.10 | 75 | ±0° | 0.75 | 15 | +1.0° | 0.73 | 17 |

*3° = 1 shutter stop

EXAMPLE 2

1.2 g of 4-hydroxy-6-methyl-1,3,3a,7-tetraazaindene in aqueous alkaline solution were added to 1 kg of a green sensitized silver iodobromide emulsion having a silver (calculated as silver nitrate)/gelatine ratio of 1:0.4 and containing 0.91 mol of silver halide per kg of emulsion having an iodide content of 5 mol percent. The resulting emulsion was divided into several equal parts and the compounds according to the present invention shown in Table 4 below were added in the given quantities as solutions in acetone or alcohol to the individual samples. Before casting, the following substances were added to the emulsion in the quantities indicated per kg:
75 g of a 5% gelatine solution;
109 g of an 11.1% coupler dispersion of the following magenta coupler:

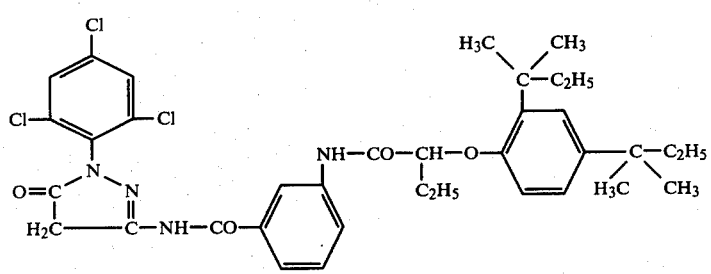

and wetting agent in aqueous solutions and 1,180 ml of water.

The emulsions were cast on a silver dispersion forming the anti-halation layer of a cellulose acetate support. The quantity of emulsion cast on each layer corresponded to a silver application of from 5.0 to 5.2 g of $AgNO_3/m^2$.

Each emulsion layer was covered with a protective layer containing a suitable hardener and a wetting agent applied in a thickness corresponding to 2 g of gelatine per $m^2$.

The samples were tested fresh and after storage in a heating cupboard at 38° C. and 60% relative humidity for 3 days.

The samples were then exposed behind a step wedge in a sensitometer and developed in the following developer II at 38° C. for 3¼ minutes.

| Developer II | |
|---|---|
| 1-hydroxyethane-1,1-diphosphonic acid-Na₂ salt | 2 g |
| ethylene diamine-N,N,N',N'—tetracetic acid | 2 g |
| potassium carbonate sicc | 34.1 g |
| sodium bicarbonate sicc | 1.55 g |
| sodium disulphite sicc | 0.28 g |
| sodium sulphite sicc | 3.46 g |
| potassium bromide | 1.34 g |
| hydroxylamine sulphate | 2.4 g |
| 4-amino-3-methyl-N—ethyl-N—(β-hydroxyethyl)-aniline | 4.7 g | made up with water to 1 liter.

The samples were then further processed in the following baths:

| Short stop bath | 1 minute at 38° C.; |
|---|---|
| Bleaching bath | 3¼ minutes at 38° C.; |
| Washing | 3½ minutes at 38° C.; |
| Fixing bath | 3¼ minutes at 38° C.; |
| Washing | 5 minutes at 38° C. |

The short stop, bleaching and fixing baths were similar to those normally used (*British Journal of Photography*, 1974, pages 597 and 598).

The results obtained are entered in Table 4.

The substances reduce the very high fog by more than 50% without reducing the sensitivity and gradation and they improve the stability of the photographic material in storage.

TABLE 4

| Compound Number | mg/kg | Test on fresh sample | | | Test after storage in heating cupboard | | |
|---|---|---|---|---|---|---|---|
| | | Sensitivity* | γ | fog | Sensitivity* | γ | fog |
| Control sample | — | 39.1 | 0.75 | 1.16 | 38.5 | 0.68 | 1.17 |
| 1.1 | 40 | −0.7° | 1.07 | 0.36 | −0.4° | 0.99 | 0.44 |
| 1.9 | 127 | ±0° | 1.03 | 0.39 | −0.1° | 1.01 | 0.47 |
| 1.10 | 149 | −0.3° | 1.09 | 0.27 | −0.1° | 1.11 | 0.31 |

*3° = 1 shutter stop.

EXAMPLE 3

125 g of a silver bromide emulsion having a high blue sensitivity and a silver nitrate content and gelatine content of 100 g/1,000 g of emulsion were melted in the presence of 7 mg of 4-hydroxy-6-methyl-1,3,3a,7-tetraazaindene dissolved in aqueous-alkaline solution, and a suitable blue sensitizer was then added. The substances according to the present invention and the comparison substances dissolved in methanol or acetone were then added in the quantities shown in Table 5. The following 2-equivalent yellow coupler:

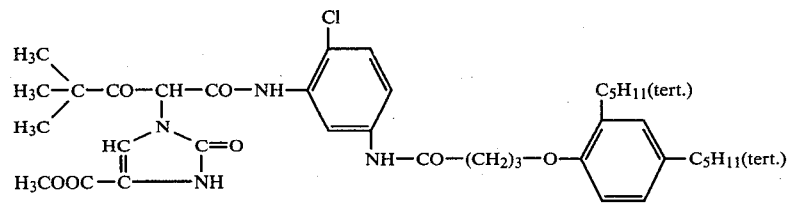

was then dissolved in tricresyl phosphate and ethyl acetate and emulsified in a gelatine solution, using di-sec.-butyl-naphthalene sulphonate, and the ethyl acetate was distilled off. This emulsion which contains ca. 5% of coupler, was then added in the quantity required to provide 18.7 g of coupler in the reaction mixture. 0.8 g of dioctyl hydroquinone in the form of tricresyl phosphate emulsion and a wetting agent were also added to the reaction mixture.

Each of these samples was applied to a substrated polyethylene coated paper in a quantity containing 0.55 g of silver calculated as $AgNO_3/m^2$. A protective layer containing 6.4 g of gelatine per $m^2$ was applied to the emulsion layer.

The layer packet was then covered with a suitable hardener.

The layers prepared as described above were exposed behind a $3\sqrt[3]{2}$ wedge and a blue filter and then developed as follows:

| Colour developer III | 33° C. | 3.5 minutes |
| --- | --- | --- |
| Bleach fix bath | 33° C. | 1.5 minutes |
| washing | 33° C. | 3 minutes |

The processing baths were prepared according to the following formulations:

| Developer III | | |
| --- | --- | --- |
| 900 | ml | water |
| 15 | ml | benzyl alcohol |
| 15 | ml | ethylene glycol |
| 3 | g | hydroxylamine sulphate |
| 4.5 | g | 3-methyl-4-amino-N—ethyl-N—(β-methane sulphonamidoethyl)-aniline sulphate |
| 32 | g | potassium carbonate sicc. |
| 2 | g | potassium sulphite sicc. |
| 0.6 | g | potassium bromide |
| 1 | g | disodium salt of 1-hydroxyethylidine-1,1 diphosphonic acid | made up with water to 1 liter and adjusted to pH 10.2.

| Bleach fix bath | | |
| --- | --- | --- |
| 700 | ml | Water |
| 35 | ml | ammonia solution (28%) |
| 30 | g | ethylene diamino-N,N,N',N'—tetracetic acid |
| 15 | g | sodium sulphite sicc |
| 100 | g | ammonium thiosulphate sicc |
| 60 | g | sodium-(ethylene diamino tetraacetate)-iron-(III)-complex | made up with water to 1 liter and adjusted to pH 7.

The yellow colour wedges were determined after development. The results obtained are entered in Table 5.

TABLE 5

| Compound | Concentration mg/100 g $AgNO_3$ | $D_{min}$ | $D_{min}$ | Sensitivity* D = 0.3 | D = 1.0 |
| --- | --- | --- | --- | --- | --- |
| Control sample | — | 0.22 | 1.67 | 6.5 | 12.0 |
| 1.1 | 20 | 0.11 | 1.63 | 9.3 | 13.0 |
| 1.2 | 100 | 0.11 | 1.62 | 9.1 | 13.5 |
| 1.4 | 50 | 0.11 | 1.62 | 8.5 | 12.3 |
| 1.8 | 40 | 0.11 | 1.62 | 8.9 | 13.1 |
| 1.9 | 100 | 0.11 | 1.65 | 8.9 | 13.1 |
| 1.10 | 100 | 0.11 | 1.72 | 8.4 | 12.5 |
| 1.11 | 100 | 0.11 | 1.69 | 9.0 | 13.0 |
| 1.13 | 50 | 0.10 | 1.59 | 8.7 | 12.3 |
| 1.14 | 150 | 0.11 | 1.67 | 8.6 | 12.1 |
| 1.24 | 100 | 0.10 | 1.73 | 8.5 | 12.3 |
| A | 50 | 0.16 | 1.40 | 14.0 | 18.5 |
| B | 100 | 0.11 | 1.53 | 13.5 | 17.4 |
| C | 200 | 0.11 | 1.70 | 11.0 | 14.9 |
| D | 60 | 0.11 | 1.65 | 8.2 | 12.5 |
| E | 100 | 0.16 | 1.55 | 14.0 | 18.0 |
| F | 50 | 0.10 | 1.56 | 12.9 | 16.1 |
| H | 30 | 0.12 | 1.56 | 9.9 | 14.0 |

*Sensitivity = xth step at density 0.3 and 1.0, respectively. The higher the numerical value, the lower is the sensitivity.

An increase in the given value by the factor $3\sqrt[3]{2}$ corresponds to a reduction in sensitivity by 1 DIN.

It may be seen very clearly that the stabilizers of the first group (1.1 to 1.24), which provide a good fog value $D_{min}$, result in a slightly depressed although still satisfactory sensitivity, while compounds of the second group (A/B/C/E/F/H) combine a satisfactory or insufficient improvement in fog value with a very strong reduction in sensitivity and are therefore unusable. Moreover, compounds D, I, J and K interfere with bleaching, as will be shown in Example 4 below.

EXAMPLE 4

This Example provides a comparison of known stabilizers containing mercapto groups with the stabilizers according to the present invention under conditions of bleaching.

A stabilizer is added in the quantity given in Table 6 (mol of stabilizer per mol of silver) to a yellow filter silver-gelatine solution and, after the addition of saponin as wetting agent, the mixture is cast on a subtrated polyethylene-coated paper support to form layers having a density of from 1.6 to 2.1.

The samples are treated in a buffer solution at pH 10 for 5 minutes, washed for 5 minutes and then immersed for one minute at 20° C. in a bleach fix bath of the following composition:
20 g Na salt of Fe III complex of ethylene diamino tetraacetic acid
10 g sodium sulphite sicc.
5 g potassium dihydrogen phosphate sicc. and 100 g ammonium thiosulphate sicc made up to 1 liter with water, pH 6.0.

The wedges are then rinsed under running water for one minute and dried. The density of the wedges are measured before and after the treatment. The results are summarised in Table 6.

TABLE 6

| Compound No. | Concentration | untreated | bleached |
|---|---|---|---|
| 1.1 | $8 \cdot 10^{-2}$ | 2.07 | 0.07 |
| 1.2 | $3.8 \cdot 10^{-2}$ | 1.82 | 0.11 |
| 1.3 | $8 \cdot 10^{-2}$ | 1.97 | 0.21 |
| 1.6 | $7.2 \cdot 10^{-2}$ | 1.87 | 0.12 |
| 1.8 | $7.5 \cdot 10^{-2}$ | 1.73 | 0.06 |
| 1.11 | $7.1 \cdot 10^{-2}$ | 1.78 | 0.05 |
| 1.15 | $3.6 \cdot 10^{-2}$ | 1.44 | 0.06 |
| 1.22 | $3.8 \cdot 10^{-2}$ | 1.59 | 0.02 |
| 1.24 | $2.8 \cdot 10^{-2}$ | 1.66 | 0.23 |
| D | $7 \cdot 10^{-2}$ | 1.93 | 2.06 |
| E | $7 \cdot 10^{-2}$ | 2.14 | 0.04 |
| H | $7 \cdot 10^{-2}$ | 1.79 | 0.09 |
| I | $7 \cdot 10^{-2}$ | 1.88 | 1.78 |
| J | $7 \cdot 10^{-2}$ | 1.91 | 2.38 |
| K | $6.8 \cdot 10^{-2}$ | 1.97 | 2.06 |
| Control Sample | — | 1.64 | 0.19 |

Comparison compounds D, I, J and K inhibit bleaching. Comparison compounds H and E which are known as bleaching accelerators resemble the compounds according to the present invention 1.1, 1.2, 1.6, 1.8, 1.11, 1.15, and 1.22 in accelerating bleaching, but, as in Example 3, they suppress the sensitivity and/or have only a slight effect in reducing fog. Compounds 1.3 and 1.24 have little or no inhibiting effect of bleaching.

EXAMPLE 5

A silver iodochlorobromide emulsion having a narrow grain size distribution prepared by the conventional method using 2% AgCl and 0.5% AgI is taken up in a gelatine solution after flocculation and washing so that the proportion of silver to gelatine is 1:1 and the emulsion contains ca. 100 g of silver halide per kg of emulsion. For ripening, the pH is adjusted to 6.5 and the pAG to 8.9. After the emulsion has been melted at 40° C., gold salts and thiosulphate are added as ripening additives. Before the emulsion is heated to the ripening temperature, it is divided into several portions. The first portion is ripened without the addition of further substances, while the substances according to the present invention dissolved in alcohols or acetone are added as ripening stabilizers in the quantities indicated in Table 7. The emulsions are ripened (ca. 100 minutes at 48° C.). The additives described in Example 3 are then added. Half of the emulsion which is then ready for casting is digested for 24 hours at 40° C. 15 ml of a 3% solution of triacryloformal and a wetting agent are added before the emulsion is cast. The resulting emulsion is then applied to a support. It is covered with a protective gelatine layer containing 1.8 g of gelatine per m² which has also been hardened with 15 ml of a 3% triacryloformal solution to 45 g of gelatine. The samples are then stored at 60° C. and 60% relative humidity for 2 days. After storage in the heating cupboard, the samples are processed in the baths indicated in Example 3.

The conditions for processing are modified as follows:

| Developer | 25° C. | 7 minutes |
|---|---|---|
| short stop bath as in | | |
| Example 1 | 20° C. | 1 minute |
| washing | cold | 1 minute |
| bleach fix bath | 20° C. | 2 minutes |
| washing | cold | 4 minutes |

The long term fogging was also determined under the following processing conditions:

| Developer | 25° C. | 5/10/15 minutes |
|---|---|---|
| short stop bath | 20° C. | 1 minute |
| washing | cold | 1 minute |
| bleach fix bath | 20° C. | 3 minutes |
| washing | cold | 4 minutes |

The wedges were exposed behind a $3\sqrt[3]{2}$ wedge and a blue filter.
The results are entered in the following Table 7.

TABLE 7

| Compound No. and quantity per 100 g of AgNO₃ | 7 minutes development time | | | Long term fog after a development time of: | | |
|---|---|---|---|---|---|---|
| | S | γ | $D_{max}$ | 5' | 10' | 15' |
| none | 100 | 1.60 | 1.88 | 0.45 | 0.49 | 0.62 |
| | 100 | 1.60 | 1.88 | 0.32 | 0.46 | 0.56* |
| 17 mg No. 1.2 | 75 | 1.75 | 1.90 | 0.14 | 0.18 | 0.28 |
| | 60 | 2.00 | 1.69 | 0.11 | 0.15 | 0.21* |
| 25 mg No. 1.2 | 70 | 1.60 | 1.82 | 0.17 | 0.15 | 0.21 |
| | 50 | 1.70 | 1.79 | 0.08 | 0.11 | 0.16* |
| 17 mg No. 1.4 | 85 | 1.80 | 1.78 | 0.14 | 0.22 | 0.32 |
| | 75 | 1.70 | 1.68 | 0.07 | 0.11 | 0.21* |
| 25 mg No. 1.4 | 80 | 1.70 | 1.85 | 0.13 | 0.17 | 0.23 |
| | 70 | 1.80 | 1.85 | 0.07 | 0.11 | 0.15* |
| 17 mg No. 1.8 | 80 | 1.70 | 1.89 | 0.13 | 0.18 | 0.24 |
| | 70 | 1.85 | 1.64 | 0.11 | 0.18 | 0.27* |
| 8 mg No. 1.10 | 90 | 1.80 | 1.78 | 0.14 | 0.22 | 0.32 |
| | 80 | 1.70 | 1.68 | 0.07 | 0.21 | 0.21* |
| 12 mg No. 1.5 | 85 | 1.75 | 1.85 | 0.25 | 0.27 | 0.30 |
| | 80 | 1.75 | 1.80 | 0.23 | 0.24 | 0.26* |
| 15 mg No. 1.22 | 75 | 1.65 | 1.70 | 0.15 | 0.19 | 0.23 |
| | 75 | 1.75 | 1.75 | 0.14 | 0.19 | 0.21* |

Results marked with * are obtained after 24 hour digestion.
S: Sensitivity at density D = 1.0

We claim:
1. Light-sensitive photographic material containing at least one light-sensitive silver halide emulsion layer and optionally other layers, wherein the improvement comprises at least one layer contains a stabilizer compound corresponding to general formula (I):

$$R^3\!\!\diagdown\!\!\underset{R^2}{\overset{}{N-N}}\!\!\diagup\!\!\!\overset{R^4\diagdown\;\;\;N\diagup N}{\underset{\|}{\quad}}\!\!-S-CO-(B)_n-(CO)_m-R^1 \qquad (I)$$

in which
R¹ denotes an optionally substituted alkyl, cycloalkyl, aryl or aralkyl group or a substituted triazole group linked via an —S— atom
R² denotes H, acyl, alkyl or —COOR⁵
R³ denotes H, acyl or —COOR⁵
R⁴ denotes H or alkyl
R⁵ denotes alkyl, cycloalkyl, aryl, aralkyl n and m, which are the same or different, denote 0 or 1 and
B denotes a divalent linking member 2. Material according to claim 1, wherein
R$^1$ is an alkyl group with 1-6 C atoms or a cycloalkyl group with 5 or 6 C atoms or a phenyl group or a benzyl group or a group of the formula

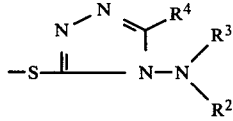

in which R$^2$-R$^4$ have the meaning indicated in claim 1 and wherein
R$^2$ is H, acetyl, alkyl with 1-4 C atoms or COOR$^5$
R$^3$ is H or an acyl group
R$^4$ denotes H or an alkyl group with 1-4 C atoms
R$^5$ denotes alkyl with 1-6 C atoms or cycloalkyl with 5 or 6 C atoms, or phenyl or benzyl
B is —O— or an organic group which can carry an oxygen atom either at one or at two positions.
3. Material according to claim 1, wherein
R$^1$ represents methyl, ethyl, isopropyl, butyl, phenyl, benzyl or a cycloalkyl group
R$^2$ represents acetyl or COOR$^5$
R$^3$ represents H or acetyl
R$^4$ represents H, methyl or ethyl
R$^5$ represents ethyl, butyl or cyclohexyl
B represents —O— or an alkylene group, an arylene group, a cycloalkylene group or an aralkylene group which organic groups can carry an oxygen atom either at one or at two positions.
4. Material according to claim 1 wherein B denotes
—O—
—O—[CH$_2$]$_p$—O— in which p=1-4
—[CH$_2$]$_p$— in which p=1-4

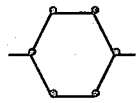

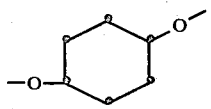

5. Material according to claim 1, wherein a compound corresponding to general formula (I) is contained in a quantity of from 5 to 500 mg per mol of silver halide.
6. Material according to claim 1, characterised in that it contains at least one of the following compounds:

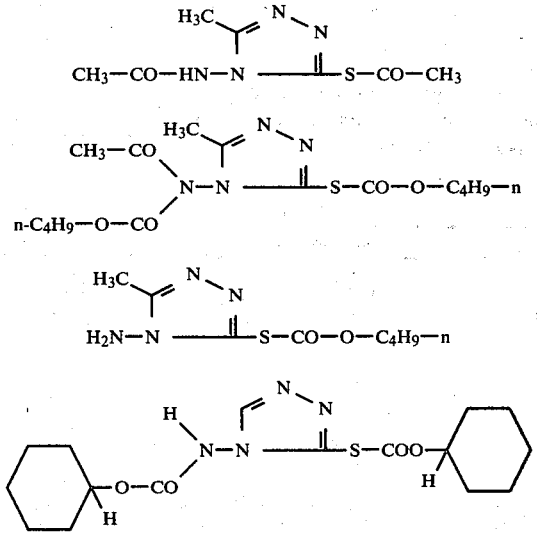

7. Process for the production of photographic images by imagewise exposure and development of the material according to claim 1.
8. In a process for stabilizing a light sensitive photographic material containing silver halide emulsion
including the preparation of the material for casting a supported layer comprising the steps of precipitating the silver halide in the presence of a protective colloid and chemical ripening the emulsion to form a casting solution
the improvement which comprises after precipitation of the silver halide and before chemical ripening, adding to the casting solution a stabilizing amount of a compound of the following formula:

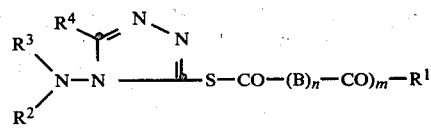
(I)

* * * * *